(12) United States Patent  
Smith

(10) Patent No.: US 8,343,408 B2
(45) Date of Patent: Jan. 1, 2013

(54) METHOD OF MOLDING AN ENDOTRACHEAL TUBE FOR TRACHEAL INTUBATION

(76) Inventor: Michael P. Smith, Copley, OH (US)

( * ) Notice: Subject to any disclaimer, the term of this patent is extended or adjusted under 35 U.S.C. 154(b) by 635 days.

(21) Appl. No.: 11/906,362

(22) Filed: Oct. 3, 2007

(65) Prior Publication Data

US 2008/0087795 A1    Apr. 17, 2008

(51) Int. Cl.
*B29C 53/08*    (2006.01)
(52) U.S. Cl. .................... 264/285; 264/295; 264/339
(58) Field of Classification Search .......... 264/259–262, 264/266, 267, 270, 285, 295, 296, 299, 313, 264/320, 322, 325, 339, 239, 241, 242, 273, 264/284; 156/156, 165; 29/469.5
See application file for complete search history.

(56) References Cited

U.S. PATENT DOCUMENTS

| | | | | |
|---|---|---|---|---|
| 3,719,737 | A * | 3/1973 | Vaillancourt et al. | 264/162 |
| 3,839,841 | A * | 10/1974 | Amplatz | 53/425 |
| RE29,343 | E * | 8/1977 | Amplatz | 53/425 |
| 4,144,632 | A * | 3/1979 | Stroupe | 29/469.5 |
| 4,292,270 | A * | 9/1981 | Hannah et al. | 264/320 |
| 5,165,540 | A * | 11/1992 | Forney | 206/364 |
| 5,259,371 | A * | 11/1993 | Tonrey | 128/200.26 |
| 5,407,613 | A * | 4/1995 | Schulte | 264/479 |
| 6,257,864 | B1 * | 7/2001 | Roberts | 425/384 |
| 6,296,801 | B1 * | 10/2001 | Teves | 264/295 |
| 2002/0056944 | A1 * | 5/2002 | Lee et al. | 264/313 |
| 2004/0104512 | A1 * | 6/2004 | Eidenschink | 264/295 |
| 2005/0029714 | A1 * | 2/2005 | Miyanaga et al. | 264/573 |

FOREIGN PATENT DOCUMENTS

| JP | 56058833 A * | 5/1981 |
|---|---|---|
| JP | 59059417 A * | 4/1984 |

* cited by examiner

*Primary Examiner* — Dimple Bodawala
(74) *Attorney, Agent, or Firm* — James A. Hudak

(57) ABSTRACT

A mold (form) in which an endotracheal tube, having a stylette therein, is received so as to form the overall configuration of the endotracheal tube is disclosed. The mold has a recess in the surface thereof to receive the endotracheal tube with a stylette therein. The recess has a curve therein adjacent one end of the mold to receive the distal end of the endotracheal tube. The recess in the opposite end of the mold has a bend therein to receive the proximal end of the endotracheal tube. The recess in the intermediate portion of the mold is substantially straight and interconnects the curved end and the oppositely disposed bent end of the recess. The stylette is fabricated from a thin metallic malleable rod which is bendable, and thus configurable, to retain the overall configuration of the endotracheal tube after being formed and removed from the mold. The stylette is withdrawn from the endotracheal tube after the distal end thereof has been inserted through the vocal cords and just into the trachea of the patient being intubated. Due to the configuration of the endotracheal tube, withdrawal of the stylette causes the distal end of the tube to advance further into the trachea of the patient being intubated.

10 Claims, 6 Drawing Sheets

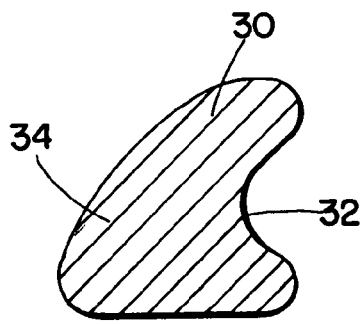 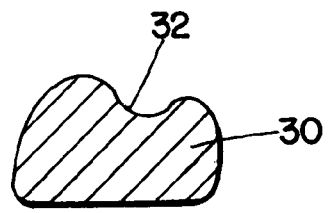
Fig. 8    Fig. 9
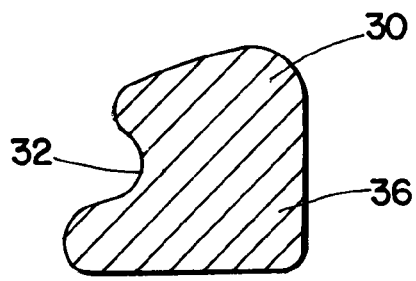
Fig. 10
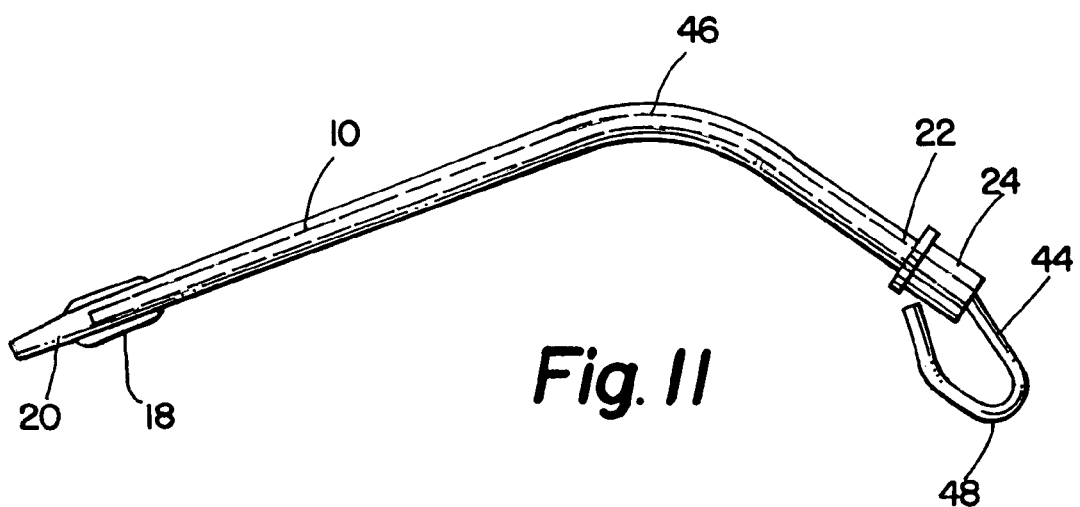
Fig. 11

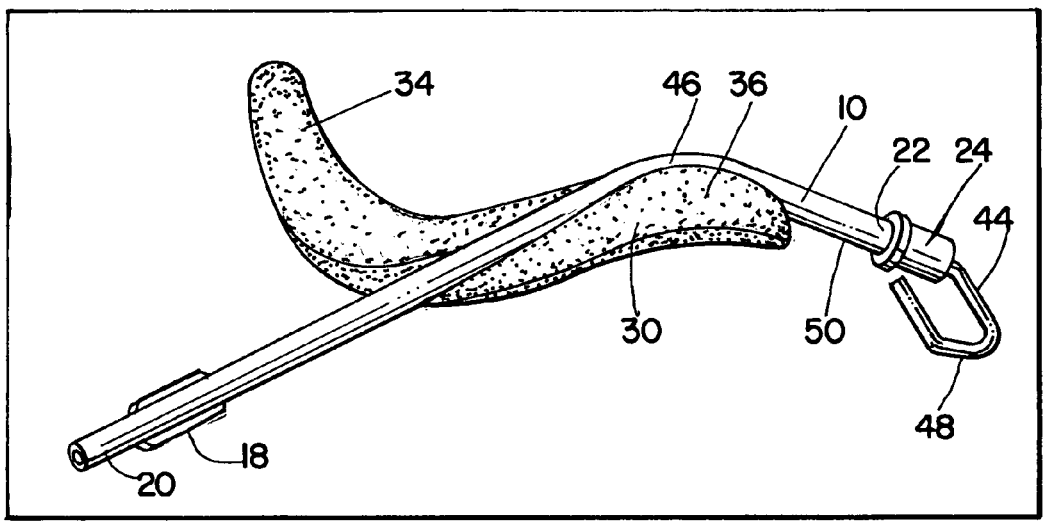
Fig. 12
Fig. 13
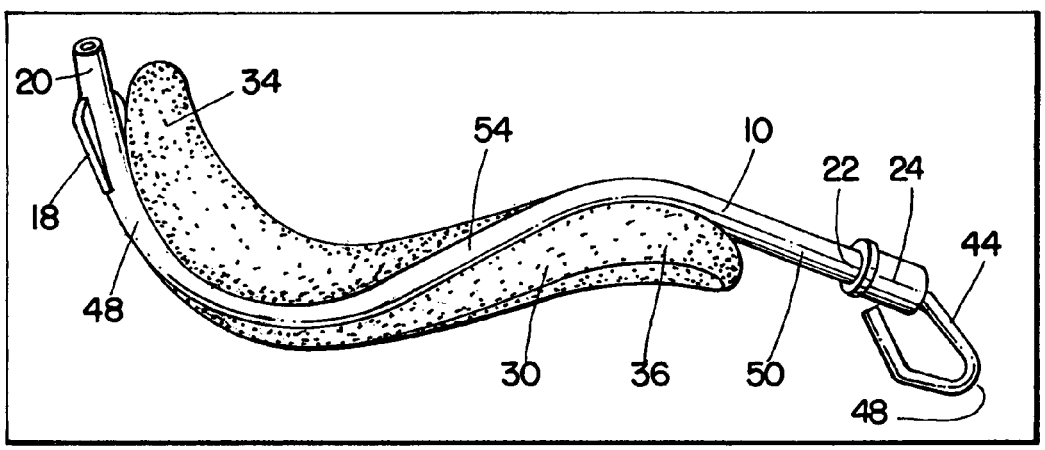
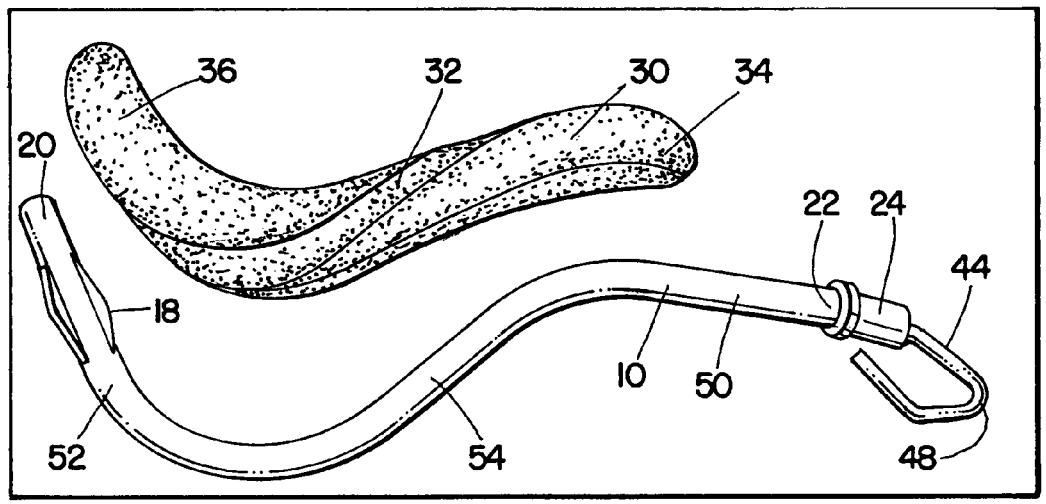
Fig. 14

METHOD OF MOLDING AN ENDOTRACHEAL TUBE FOR TRACHEAL INTUBATION

TECHNICAL FIELD

The present invention relates, in general, to the field of endotracheal intubation and, more particularly, to a mold utilized to configure a styletted endotracheal tube to provide an improved method of intubation. The method is suitable for all endotracheal tube placements including those utilizing non-direct line of sight intubation techniques, such as video laryngoscopic or transillumination light wand techniques, wherein the endotracheal tube incorporates a malleable metallic stylette.

BACKGROUND OF THE INVENTION

Endotracheal intubation is a routine life preserving procedure with application in a vast number of settings. Situations in which a patient's airway needs to be secured with an endotracheal tube are numerous and include tracheal intubation in a patient when undergoing a general anesthetic or when the patient requires prolonged treatment in an intensive care unit or is subjected to a field emergency where the patient's status may need to be further clarified in the hospital.

A secure, reliable airway for the patient is of paramount importance. A patient who requires ventilatory support for survival is dependent on the timely and accurate placement of an endotracheal tube within his or her trachea. Safe and expedient endotracheal tube placement is therefore of the highest priority both in the operating room as well as other settings in which the patient is unable to adequately oxygenate and ventilate.

With that goal in mind, the American Society of Anesthesiology (ASA) has undertaken research and educational efforts to promote safe endotracheal intubation. The much-cited ASA "Closed Claims" study revealed the serious consequences of the inability to secure a patient's airway. Indeed, the study showed that nearly 17% of all claims against anesthesiologists were due to "difficult" intubations. Distressingly, since 1992, up to one third of all anesthesia related deaths during operating procedures have been due to failed intubations.

During the routine intubation of an otherwise healthy individual, the practitioner has the relative comfort of time on his or her side. The patient is initially examined and a pre-intubation assessment of difficulty is made with regard to intubation. If the patient's clinical airway assessment is unremarkable, pre-oxygenation is carried out, anesthetic medications are administered and then mask ventilation of the patient is initiated. Assuming the patient is easily ventilated, the practitioner proceeds with administering a muscle relaxant and then proceeds with direct laryngoscopy and endotracheal tube placement.

Unfortunately, not all tracheal intubations proceed as smoothly as the above description. In fact, approximately 3-18% of all intubations carried out under routine anesthesia can be classified as "difficult" intubations. A difficult intubation has been defined as one in which three attempts by an experienced practitioner fails to yield successful placement of an endotracheal tube. While the pre-operative examination can offer important indications as to a possible difficult intubation, factors such as neck size, Mallampati view, neck extension, and mouth opening are only partially predictive of a difficult intubation. Therefore, the very real possibility of the dreaded unknown/unanticipated difficult airway is a situation in which every practitioner must be able to successfully handle.

In the foregoing scenario, the proficient, reproducible use of the non-direct laryngoscopic technique is paramount. One particular type of non-direct laryngoscopic technique utilizes a video laryngoscope, such as the GlideScope produced by the Saturn Biomedical System, Inc., Burnaby, British Columbia, Canada. This device has been shown by multiple studies to provide improved glottic views (Cormack-Lehane) in both simulated easy and difficult airways when compared to the use of Macintosh (direct) laryngoscopy. A commonly cited difficulty in the successful use of the GlideScope is in timely and efficient placement of the endotracheal tube once the glottis has been visualized. One method for successful intubation, as stated in the literature and advised by the manufacturer, recommends that the styletted endotracheal tube have an angulated tip so as to match the 60 degree angulation of the GlideScope blade. An alternate method utilizes a styletted endotracheal tube in the shape of an "L" or commonly known as a "hockey stick". In many instances of difficult intubation with the videolaryngoscope, the primary obstacle is not visualization of the glottic anatomy, but rather the difficulty in successfully placing the endotracheal tube through the vocal cords. A commonly encountered difficulty in this respect is the positioning of the endotracheal tube tip in the vertical plane just prior to passing it through the vocal cords. Another common difficulty is the inability to advance the endotracheal tube through the vocal cords and into the trachea. Thus, the overall configuration of the endotracheal tube is of paramount importance in obtaining a successful intubation.

Historically, when a stylette is used to facilitate intubation, the styletted endotracheal tube is formed into the aforementioned "hockey stick" configuration. However, this shape is fundamentally flawed for positioning of the distal end of the endotracheal tube through the vocal cords. Although the tip of the endotracheal tube may finally be maneuvered to the vocal cords, it is common for the practitioner to have difficulty advancing the endotracheal tube through the vocal cords and into the trachea due to the "L shaped" bend involved causing the tip of the endotracheal tube to drag or stick on the anterior rings of the trachea. This "hockey stick" configuration also results in the common occurrence of inadvertent extubation (endotracheal tube falling out of the patient's trachea) upon the withdrawal of the stylette from the lumen of the endotracheal tube.

Various patents have been directed to forming the configuration of the endotracheal tube to assist in the intubation process. For example, the Gomez reference (U.S. Pat. No. 6,053,166) is directed to an intubation assembly having a guide assembly that receives the intubation tube therein and conforms the configuration of the intubation tube. The guide assembly includes a first segment and a second segment that are hingedly coupled to one another and positionable between a closed position which defines a curved configuration of the guide assembly and an open position which defines a straight configuration of the guide assembly.

The Schwartz reference (U.S. Pat. No. 6,539,942) discloses a device for facilitating intubation comprising a tube that is inserted into an endotracheal tube. The device includes a control wire and handgrip to curve the distal end of the device into the desired configuration via a series of interlinked, ring-like elements disposed along the distal end of the tube. The amount of force applied to the handgrip controls the degree of bend achieved in the distal end of the device.

The Toti, et. al. reference (U.S. Pat. No. 6,321,749) discloses an endotracheal tube having a portion thereof that can be bent during intubation so as to control the position of the distal end of the tube. The distal end of the endotracheal tube is configured by means of a wire which is received within the endotracheal tube and which can be pulled causing the distal end of the tube to be curved or bent for placement in the trachea of the person being intubated.

The Raspallo reference (U.S. Pat. No. 6,874,504) discloses an endotracheal tube having a proximal tube shaft, which is coupled to a distal tube shaft. The distal tube shaft includes two or more curved portions configured to be inserted into the trachea when the tube is inserted into the person being intubated. An inflatable cuff covers at least a portion of the two or more curved portions of the distal end of the endotracheal tube.

The Parker reference (U.S. Pat. No. 5,174,283) discloses a guide member having a channel therein for the receipt of an orotracheal tube. The guide member is positioned atop the larynx such that the wall of the channel forms an upward continuation of the laryngeal wall. The orotracheal tube is advanced through the channel into the larynx and trachea preventing the accidental intubation of the esophagus.

All of the devices in the foregoing references are rather complex and, due to their structure and/or operation, have certain inherent operational disadvantages. Many of these devices cannot be used in conjunction with videolaryngoscopy due to the limited space in the patient's mouth. Thus, these devices cannot take advantage of an excellent proven means for visualizing the vocal cords. Also, many of these devices cannot be used in conjunction with routine direct laryngoscopy which is the standard method of endotracheal intubation. Many practitioners routinely use a styletted endotracheal tube with the fundamentally flawed "hockey stick" configuration due to the inability to reliably, easily and effectively reproduce other styletted endotracheal tube configurations. Ideally, the device should not only allow the formation of bends in the endotracheal tube but would also provide the ability to form readily reproducible curves given that the normal anatomy of the tongue is more curved than straight. Such curves would also provide additional desirable mechanical features not only for maneuvering the endotracheal tube in the patient's mouth, but also for advancing the tube through the vocal cords into the trachea. The styletted endotracheal tube, with curves therein, would also have a mechanical advantage of not extubating the trachea, as commonly occurs with the tube when in the "hockey stick" configuration. In contrast, due to the configuration of the formed endotracheal tube, withdrawal of the curved, formed stylette from the endotracheal tube causes the distal end of the endotracheal tube to advance further into the trachea of the patient being intubated.

With this in mind, it has become desirable to develop a mold (form) to reliably and easily configure a styletted endotracheal tube having bends and curves therein so as to assist the practitioner in the insertion of the distal end of same through the vocal cords and into the trachea of the patient during the intubation process. It is apparent from the foregoing that teaching the technique of intubation is difficult and standardizing a variable, such as forming the configuration of the endotracheal tube utilizing such a mold, will provide a faster learning curve for those being taught the technique of intubation.

SUMMARY OF THE INVENTION

The present invention solves the problems associated with the prior art methods and devices for forming the distal end of an endotracheal tube so as to assist in the insertion of same through the vocal cords and into the trachea of the patient during the intubation process, and other problems, by providing a mold (form) in which an endotracheal tube, having a stylette therein, is received so as to form the overall configuration of the endotracheal tube. The mold has a recess therein to receive the endotracheal tube and stylette. Adjacent one end of the mold is a curve to receive the distal end of the endotracheal tube. The opposite end of the mold has a bend therein to receive the proximal end of the endotracheal tube. An intermediate portion of the mold is substantially straight and interconnects the curved end (distal end) and the oppositely disposed bent end (proximal end) of the recess. The stylette which is received within the endotracheal tube is fabricated from a thin metallic malleable rod which is bendable, and thus configurable, to retain the desired overall configuration of the endotracheal tube after being formed within the recess and removed from the mold. The stylette is withdrawn from the endotracheal tube after the distal end thereof has been inserted through the vocal cords and just into the trachea of the patient being intubated. Due to the configuration of the endotracheal tube, withdrawal of the stylette causes the distal end of the tube to advance further into the trachea of the patient being intubated.

BRIEF DESCRIPTION OF THE DRAWINGS

FIG. 8 is a cross-sectional view of the mold taken across section-indicating lines 8-8 in FIG. 3.
FIG. 9 is a cross-sectional view of the mold taken across section-indicating lines 9-9 in FIG. 3.
FIG. 10 is a cross-sectional view of the mold taken across section-indicating lines 10-10 in FIG. 3.
FIG. 11 is a front elevational view of an endotracheal tube prior to being formed into the desired configuration for the intubation process.
FIG. 12 is a front elevational view of the mold of the present invention and the endotracheal tube at the start of the process to form the endotracheal tube into the desired configuration for the intubation process and illustrates the forming of the bend in the endotracheal tube adjacent its proximal end.
FIG. 13 is a front elevational view of the mold of the present invention and the endotracheal tube at the completion of the process to form the endotracheal tube into the desired configuration for the intubation process and illustrates the forming of the curve in the endotracheal tube adjacent its distal end and the substantially straight intermediate portion of the endotracheal tube which interconnects its distal end with its proximal end.
FIG. 14 is a front elevational view of the mold of the present invention and the endotracheal tube and illustrates the desired configuration of the endotracheal tube for the intubation process at the completion of the process of being formed.

DESCRIPTION OF THE PREFERRED EMBODIMENT

Figure 1:
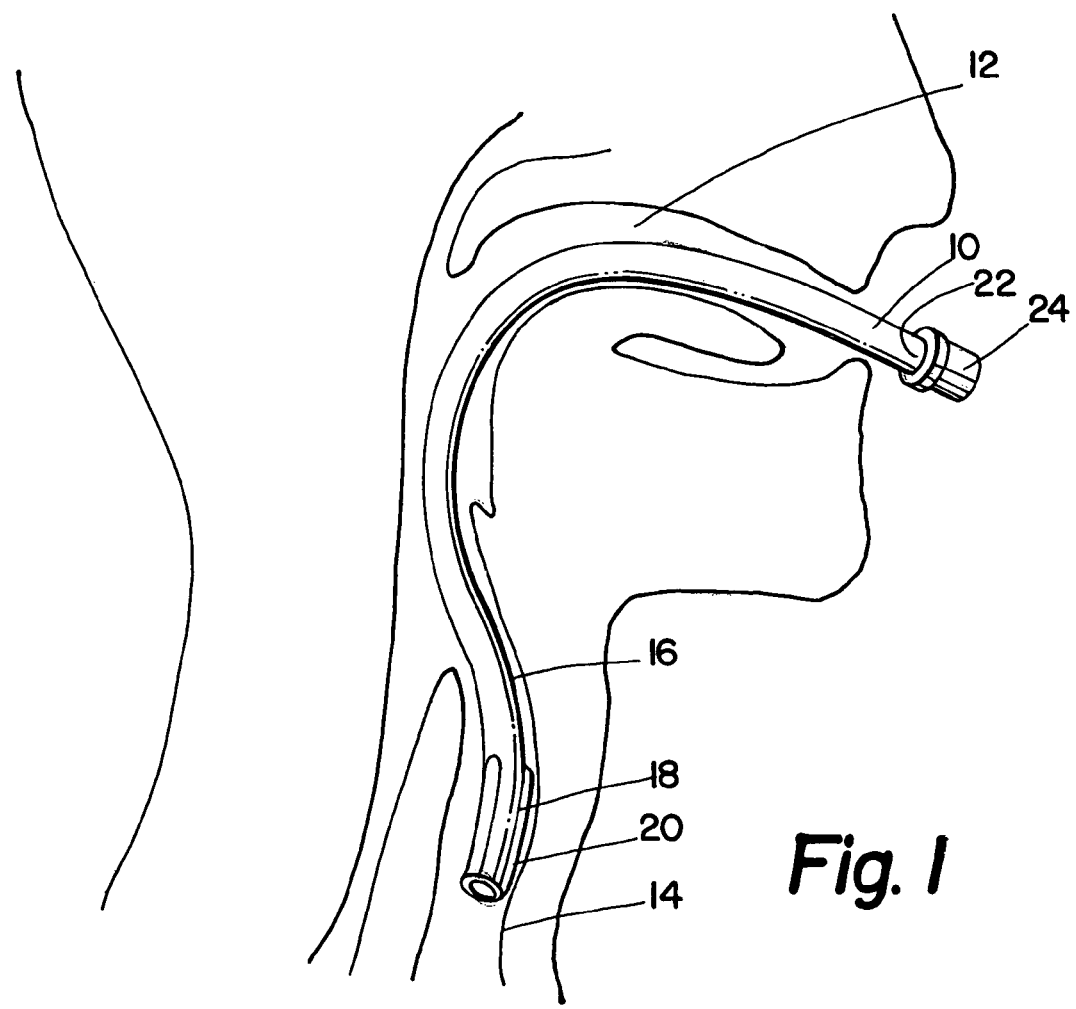
FIG. 1 is a cross-sectional view illustrating the position of a properly configured endotracheal tube within the mouth and trachea of the patient being intubated.

Referring now to the drawings where the illustrations are for the purpose of describing the preferred embodiment of the present invention and are not intended to limit the invention described herein, FIG. 1 is a partial cross-sectional view illustrating the position of a properly configured endotracheal tube 10 within the mouth 12 and trachea 14 of the patient being intubated. The endotracheal tube 10 is formed from a flexible plastic or latex material and has a hollow tubular body 16 with an inflatable balloon 18, also referred to as a cuff, mounted on the external surface of the body 16 near the distal end 20 thereof. Connected to the space between the tubular body 16 and the balloon 18 is a supply line (not shown) that runs from the proximal end 22 of the tubular body 16 to the distal end 20 of the tubular body 16. The supply line is utilized to inflate the balloon 18 to a desired diameter once the endotracheal tube 10 has been placed in its desired location in the air passage of a patient being intubated. The supply line is typically a small diameter tube that runs through a passageway (not shown) within the wall of the tubular body 16, or along the inner or outer surface of the wall. A valve (not shown) is provided on the proximal end of the tube and acts to retain inflation air in the balloon. A stylette (not shown) is received within the tubular body 16 and runs from the proximal end 22 of the tubular body 16 to the distal end 20 thereof. The stylette is formed from a thin metallic malleable rod which is bendable, and thus configurable, to retain the desired overall configuration of the endotracheal tube 10 after being formed and removed from the mold, hereinafter described. An adapter 24 is provided on the proximal end 22 of the tubular body 16 permitting the attachment of the tubular body 16 to a source of air, oxygen, or a gaseous anesthetic mixture. The distal end 20 of the tubular body 16 is open to allow gas provided into the proximal end 22 of the tubular body 16 to flow therethrough without obstruction into the patient's trachea 14.

Routinely, the stylette is withdrawn from the endotracheal tube 10 after the distal end 20 of the tubular body 16 has been inserted through the vocal cords and just into the trachea of the patient being intubated. It is desirable that the styletted endotracheal tube have a configuration so as to result in the advancement of the tip of the distal end 20 of the endotracheal tube 10 further into the trachea as the stylette is being withdrawn, while specifically avoiding the undesirable event of pulling out the endotracheal tube 10 during the withdrawal process. In addition, it is desirable that the styletted endotracheal tube be configured into an ergonomic shape so as to assist the practitioner in maneuvering the endotracheal tube 10 through the pharyngeal cavity to the location of the vocal cords.

Figure 2:
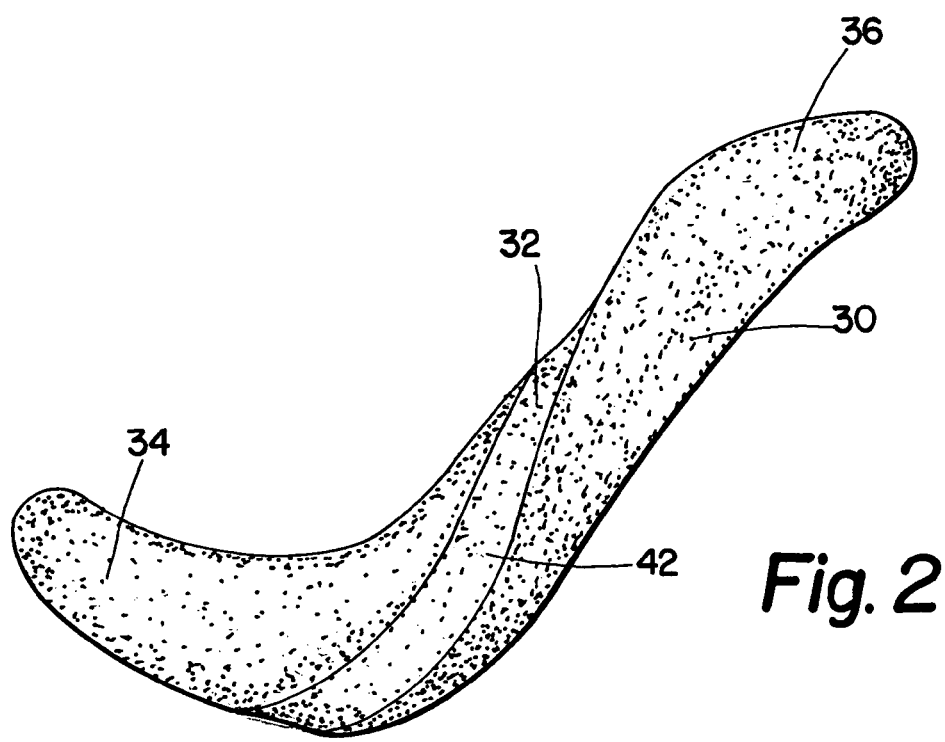
FIG. 2 is a perspective view of the mold of the present invention that is utilized to form an endotracheal tube into the desired configuration for the intubation process.
Figure 3:
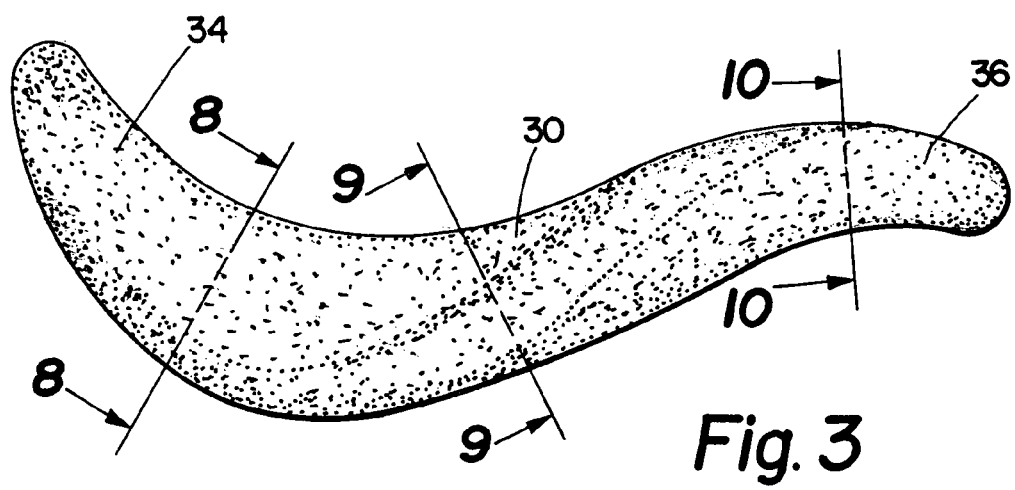
FIG. 3 is a top view of the mold of the present invention that is utilized for form an endotracheal tube into the desired configuration for the intubation process.
Figure 4:
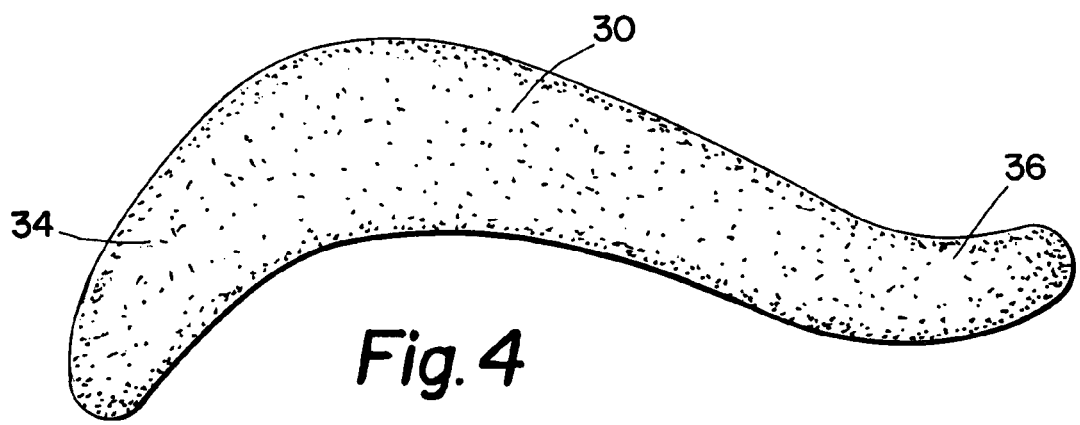
FIG. 4 is a bottom view of the mold illustrated in FIG. 3.
Figures 5, 6:
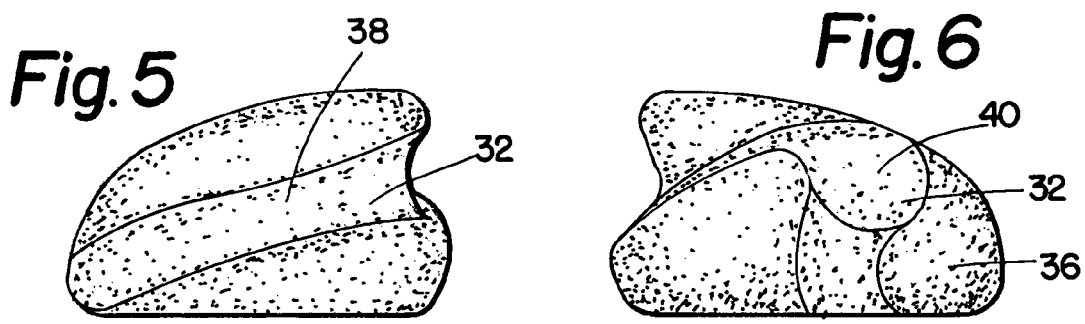
FIG. 5 is a left end view of the mold illustrated in FIG. 3.
FIG. 6 is a right end view of the mold illustrated in FIG. 3.
Figure 7:
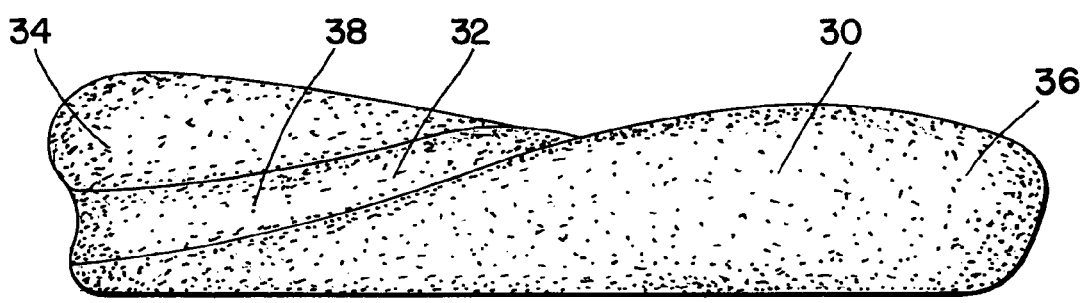
FIG. 7 is a front elevational view of the mold illustrated in FIG. 3.

Referring now to FIG. 2, a perspective view of the mold 30 of the present invention utilized to form the endotracheal tube 10 into the desired configuration for the intubation process is illustrated. Additional views of mold 30 are shown in FIGS. 3-10. The mold 30 is typically formed from a moldable plastic or polymeric material and has a semicircular continuous recess 32 in the surface thereof. Alternatively, the mold 30 can be formed from metallic material, such as a casting, stamping, or tubular structure, or can be formed from wood. The recess 32 runs from the distal end 34 to the proximal end 36 of the mold 30. The recess 32 is sized so as to receive the tubular member 16 of endotracheal tube 10 and is configured so as to form the endotracheal tube 10 into the desired configuration for the intubation process. As such, a curve, shown generally by the numeral 38, is provided in the recess 32 adjacent the distal end 34 of the mold 30 so as to provide a curve in the distal end 20 of the tubular member 16 forming the endotracheal tube 10. Similarly, a bend, shown generally by the numeral 40, is provided in the recess 32 adjacent the proximal end 36 of the mold 30 so as to provide a bend in the proximal end 22 of the tubular member 16 forming the endotracheal tube 10. The portion 42 of the recess 32 interconnecting the curved portion 38 of the recess 32 adjacent the distal end 34 of the mold 30 and the bend portion 40 of the recess 32 adjacent the proximal end 36 of the mold 30 is substantially straight. The recess 32 may have indicia markings therein (not shown) to assist in the forming the desired configuration of the endotracheal tube 10 hereinafter described.

Referring now to FIG. 11, a front elevational view of an endotracheal tube 10 prior to being formed into the desired configuration for the intubation process is illustrated. The endotracheal tube 10 has a stylette 44 therein to maintain its shape or configuration and a bend 46 therein adjacent its proximal end 22. The included angle forming bend 46 is approximately 135 degrees. The proximal end 48 of the stylette 44 is formed into a hook configuration to permit the grasping of same for removal thereof from the tubular body 16 after the placement of the distal end 20 of the tubular body 16 adjacent the vocal cords of the patient being intubated. Referring now to FIG. 12, a front elevational view of the endotracheal tube 10 at the start of the process of being formed into the desired configuration for the intubation process is illustrated. In this Figure, the bend portion 46 of the endotracheal tube 10 adjacent its proximal end 22 is placed in the bend portion 40 of the recess 32 in the mold 30 and is manually pressed therein to properly form the proximal end portion 50 of the endotracheal tube 10. The remainder of the endotracheal tube 10 is then manually pressed into the recess 32 in the mold 30 so as to form the distal end portion 52 and the intermediate portion 54 of the endotracheal tube 10, which interconnects the distal end portion 52 with the proximal end portion 50 thereof, as shown in FIG. 13. This Figure illustrates a front elevational view of the mold 30 and the endotracheal tube 10 at the completion of the process to form the endotracheal tube 10 into the desired configuration for the intubation process. FIG. 14 is a front elevational view of the mold 30 with the endotracheal tube 10 having been removed from the recess 32 therein and illustrates the resulting desired configuration of the endotracheal tube 10 for the intubation process after being formed utilizing the mold 30 of the present invention.

Figure 15:
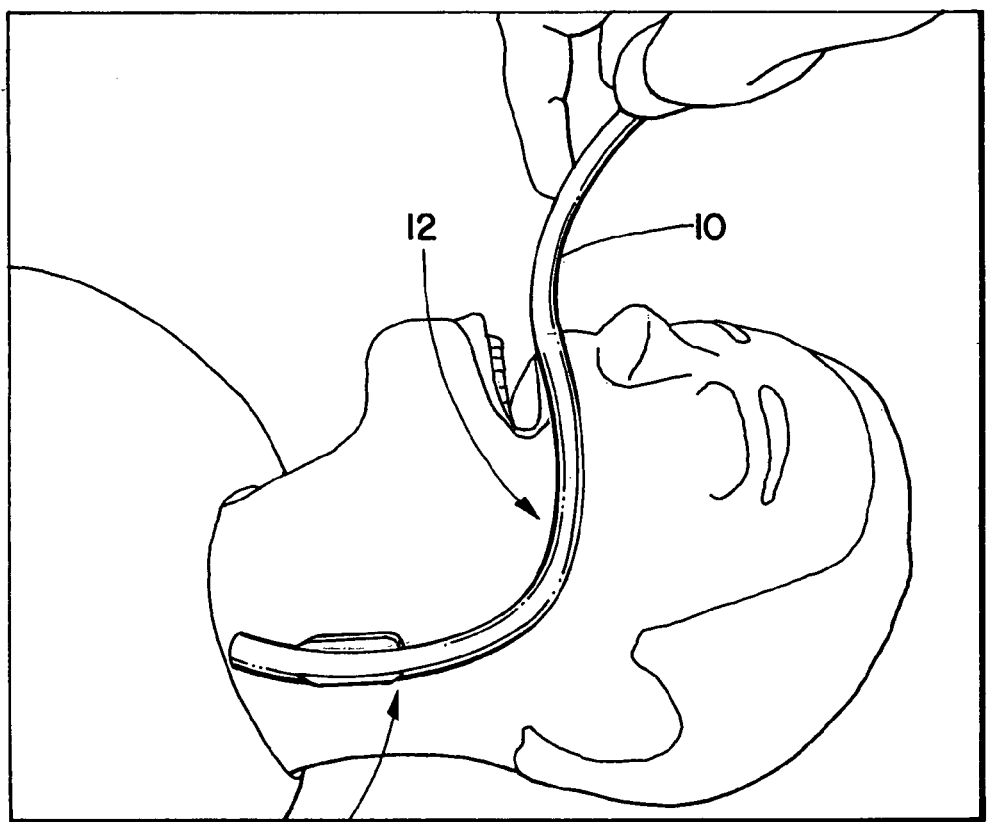
FIG. 15 is a perspective view illustrating the position of the endotracheal tube within the mouth and the trachea of the patient at the completion of the intubation process.
Figure 16:
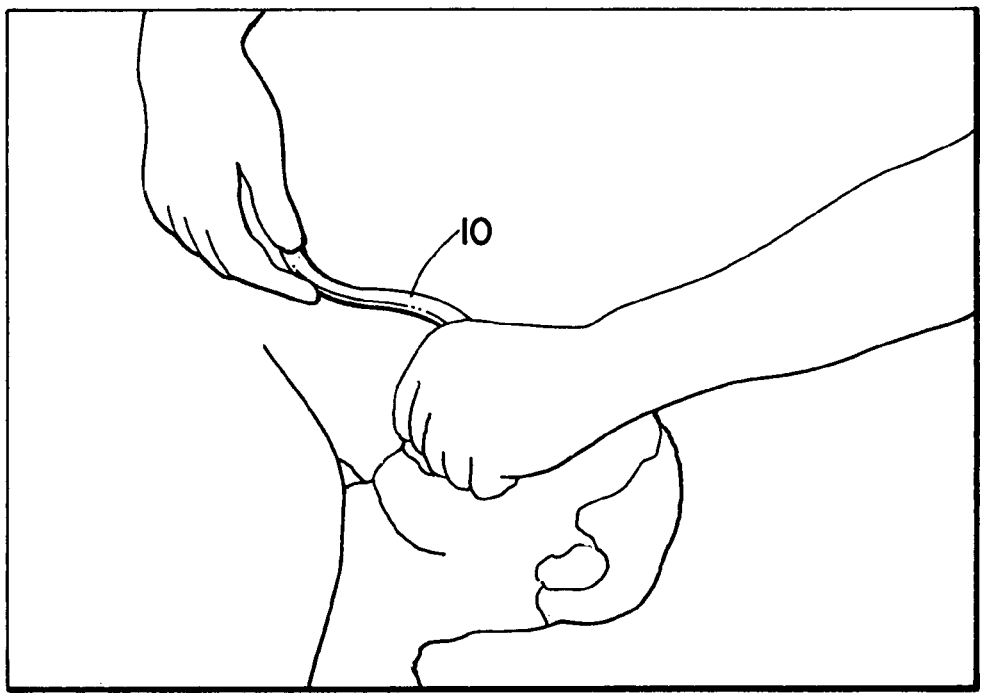
FIG. 16 is a perspective view of a patient being intubated and the endotracheal tube that has been formed into the desired configuration at the start of the intubation process.
Figure 17:
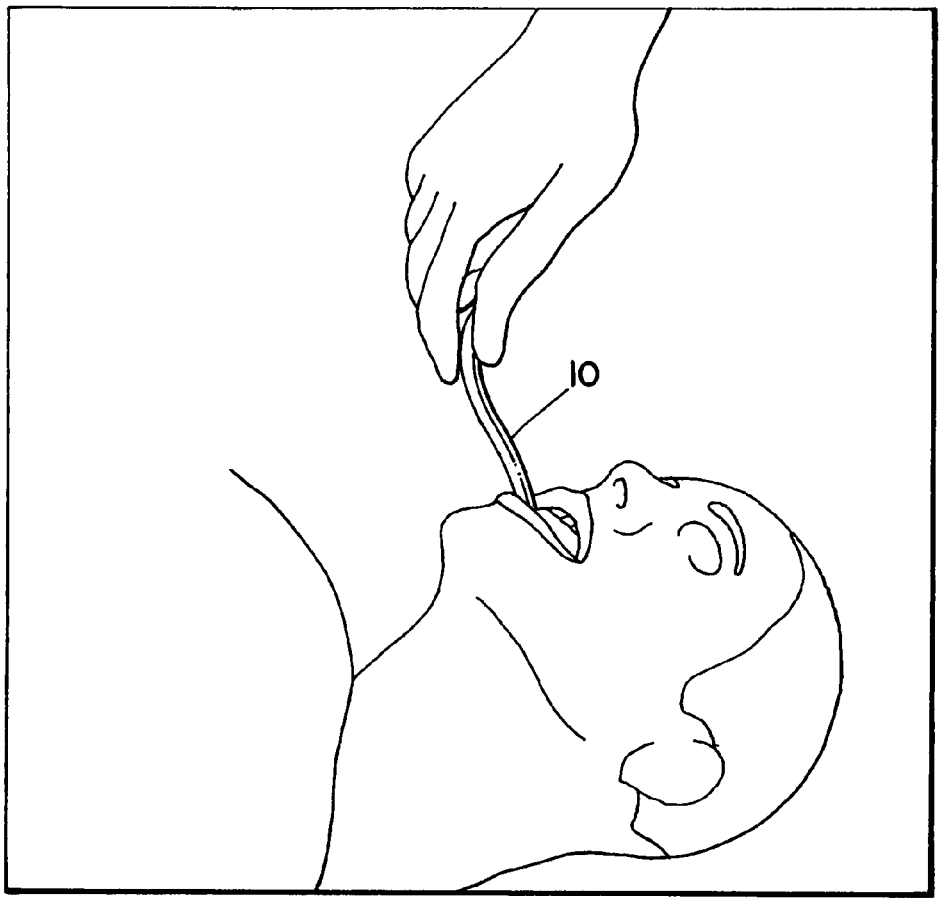
FIG. 17 is a perspective view of a patient being intubated and the endotracheal tube that has been formed into the desired configuration at the completion of the intubation process.
Figure 18:
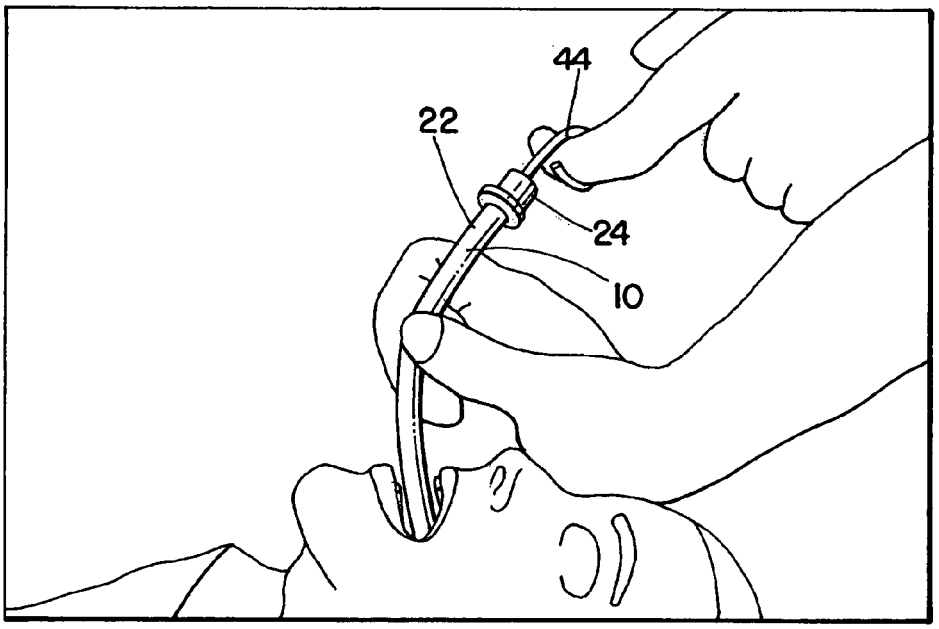
FIG. 18 is a perspective view of a patient who has been intubated with an endotracheal tube that has been formed into the desired configuration at the completion of the intubation process and illustrates the removal of the stylette from the endotracheal tube.

Referring now to FIG. 15, a perspective view of the position of an endotracheal tube 10 that has been formed into the desired configuration for the intubation process by the use of the mold 10 and having been received within the mouth 12 and trachea 14 of the patient being intubated is illustrated. FIG. 16 is a perspective view of a patient being intubated with an endotracheal tube 10 that has been formed into the desired configuration by the use of the mold 30 and illustrates the position of the endotracheal tube 10 at the start of the intubation process. Referring now to FIG. 17, a perspective view of a patient being intubated with an endotracheal tube 10 that has been formed into the desired configuration by the use of mold 30 is illustrated and shows the position of the endotracheal tube 10 at the completion of the intubation process. FIG. 18 is a perspective view of a patient who has been intubated with an endotracheal tube 10 that has been formed into the desired configuration by the use of mold 30 and illustrates the removal of the stylette 44 from the endotracheal tube 10 at the completion of the intubation process. As the stylette 44 is withdrawn from the tubular body 16, the distal end 20 of the tubular body 16 advances further into the trachea of the patient being intubated. This advancement of the distal end 20 of the tubular body 16 further into the trachea is caused by the lateral movement of the stylette 44, which has been formed into the desired configuration of the endotracheal tube 10, within the tubular body 16.

From the foregoing, it is apparent that placement of an endotracheal tube is a relatively routine procedure that is carried out millions of time each year in locations as diverse as an operating room or the back of an ambulance. Encountering a difficult intubation is not an uncommon occurrence for the provider of life support in the aforementioned venues. With the technological advancement in videolaryngoscopy technology, the practitioner has additional devices available to overcome the problems associated with a difficult intubation. Despite these advancements, lack of a reproducible, consistent approach to overcoming the problems associated with the successful placement of an endotracheal tube after glottic visualization still exists when a videolaryngoscope is used. The mold 30 of the present invention provides a rapid and easy method to configure an endotracheal tube 10 into the desired configuration so that when a difficult air passageway is encountered, the provider can quickly convert an improved glottic view using the videolaryngoscopic into a secured air passageway. As a result, more difficult air passageways will be securely connected to artificial ventilation, thus minimizing deleterious episodes of hypoxia and all the subsequent morbidities associated therewith. In addition, the teaching of the technique of intubation is difficult and standardizing a variable, such as forming the configuration of the endotracheal tube 10 using the mold 30 of the present invention, provides a faster learning curve for those being taught the technique of intubation. It should be noted that the mold 10 of the present invention is shown herein as being in a one-piece solid shape having a recess in the surface thereof. It is understood that the mold could be in the form of a two-piece hinged construction having mating semi-circular portions of the recess therein. Additionally, the overall length of the mold could be adjustable through the use of interchangeable components.

Certain modifications and improvements will occur to those skilled in the art upon reading the foregoing. It is understood that all such modifications and improvements have been deleted herein for the sake of conciseness and readability, but are properly within the scope of the following claims.

I claim:

1. A method of forming the overall configuration of a flexible plastic or latex endotracheal tube having a metallic, bendable stylette therein, said endotracheal tube having a first portion, an oppositely disposed second portion, and an intermediate portion interconnecting said first portion and said second portion through the use of an open mold member having a first end, an oppositely disposed second end and an intermediate portion interconnecting said first end and said second end, said open mold member having a substantially semi-circular continuous recess located around an outer surface of said open mold member such that said recess extends from said first end to said second end, said recess having a first portion substantially adjacent said first end of said open mold member, a second portion substantially adjacent said second end of said open mold member and an intermediate portion interconnecting said first portion and said second portion of said recess, comprising the steps of:
   a) receiving said first portion of said endotracheal tube in said first portion of said recess in said open mold member so as to substantially form said first portion of said endotracheal tube to the configuration of said first portion of said recess;
   b) wrapping said endotracheal tube around said open mold member so as to substantially align said intermediate portion of said endotracheal tube with said intermediate portion of said open mold member;
   c) receiving said intermediate portion of said endotracheal tube in said intermediate portion of said recess in said open mold member so as to substantially form said intermediate portion of said endotracheal tube to the configuration of said intermediate portion of said recess;
   d) wrapping said endotracheal tube around said open mold member so as to substantially align said second portion of said endotracheal tube with said second portion of said open mold member;
   e) receiving said second portion of said endotracheal tube in said second portion of said recess in said open mold member so as to substantially form said second portion of said endotracheal tube to the configuration of said second portion of said recess; and
   f) removing said endotracheal tube from said recess in said open mold member.

2. The method as defined in claim 1 wherein said first portion of said recess in said open mold member has a curve therein to configure a curve in the distal end of said endotracheal tube.

3. The method as defined in claim 1 wherein said second portion of said recess in said open mold member has a bend therein to configure a bend in the proximal end of said endotracheal tube.

4. The method as defined in claim 1 wherein said first portion of said recess in said open mold member has a bend therein to configure a bend in the proximal end of said endotracheal tube.

5. The method as defined in claim 1 wherein said second portion of said recess in said open mold member has a curve therein to configure a curve in the distal end of said endotracheal tube.

6. A method of forming the overall configuration of a flexible plastic or latex endotracheal tube having a metallic, bendable stylette therein, said endotracheal tube having a first portion, an oppositely disposed second portion, and an intermediate portion interconnecting said first portion and said second portion through the use of an open mold member having a first end, an oppositely disposed second end and an intermediate portion interconnecting said first end and said second end, said open mold member having a substantially semi-circular continuous recess located around an outer surface of said open mold member such that said recess extends from said first end to said second end, said recess having a first portion substantially adjacent said first end of said open mold member, a second portion substantially adjacent said second end of said open mold member and an intermediate portion interconnecting said first portion and said second portion of said recess, comprising the steps of:
  a) receiving said intermediate portion of said endotracheal tube in said intermediate portion of said recess in said open mold member so as to substantially form said intermediate portion of said endotracheal tube to the configuration of said intermediate portion of said recess;
  b) wrapping said endotracheal tube around said open mold member so as to substantially align said first portion of said endotracheal tube with said first portion of said open mold member;
  c) receiving said first portion of said endotracheal tube in said first portion of said recess in said open mold member so as to substantially form said first portion of said endotracheal tube to the configuration of said first portion of said recess;
  d) wrapping said endotracheal tube around said open mold member so as to substantially align said second portion of said endotracheal tube with said second portion of said open mold member;
  e) receiving said second portion of said endotracheal tube in said second portion of said recess in said open mold member so as to substantially form said second portion of said endotracheal tube to the configuration of said second portion of said recess; and
  f) removing said endotracheal tube from said recess in said open mold member.

7. The method as defined in claim 6 wherein said first portion of said recess in said open mold member has a curve therein to configure a curve in the distal end of said endotracheal tube.

8. The method as defined in claim 6 wherein said second portion of said recess in said open mold member has a bend therein to configure a bend in the proximal end of said endotracheal tube.

9. The method as defined in claim 6 wherein said first portion of said recess in said open mold member has a bend therein to configure a bend in the proximal end of said endotracheal tube.

10. The method as defined in claim 6 wherein said second portion of said recess in said open mold member has a curve therein to configure a curve in the distal end of said endotracheal tube.

* * * * *